United States Patent [19]

Haag et al.

[11] Patent Number: 5,008,482

[45] Date of Patent: Apr. 16, 1991

[54] DIRECT PRODUCTION OF STYRENES BY REACTION OF AROMATICS WITH ALDEHYDES

[75] Inventors: Werner O. Haag, Lawrenceville, N.J.; Rudolph M. Lago, Yardley, Pa.

[73] Assignee: Mobil Oil Corp., Fairfax, Va.

[21] Appl. No.: 456,704

[22] Filed: Dec. 26, 1989

[51] Int. Cl.$^5$ ............................ C07C 1/20; C07C 1/32
[52] U.S. Cl. ..................................... 585/437; 585/469
[58] Field of Search .......................................... 585/437

[56] References Cited

U.S. PATENT DOCUMENTS 4,827,065  5/1989  Shimuzu et al. .................... 585/319

Primary Examiner—Curtis R. Davis
Attorney, Agent, or Firm—Alexander J. McKillop; Charles J. Speciale; Edward F. Kenehan, Jr.

[57] ABSTRACT

There is provided a process for producing a styrenic compound by reacting an aromatic compound with an aldehyde over an intermediate pore size molecular sieve catalyst. Such styrenic compounds include unsubstituted styrene and substituted styrene. Examples of such aromatic compounds include unsubstituted benzene and alkylbenzenes. An example of such an aldehyde is acetaldehyde. An example of such a catalyst is a ZSM-5 catalyst.

6 Claims, No Drawings

DIRECT PRODUCTION OF STYRENES BY REACTION OF AROMATICS WITH ALDEHYDES

BACKGROUND

There is provided a process for producing a styrenic compound by reacting an aromatic compound with an aldehyde over an intermediate pore size molecular sieve catalyst, such as a ZSM-5 catalyst.

There are several established ways to produce styrenes. Styrene is obtained by the dehydrogenation of ethylbenzene; p-methylstyrene can similarly be obtained from p-methylethylbenzene (p-ethyltoluene). This method, however, is not suitable when larger or reactive substituents are present. For example, n-propyl styrene can not be prepared by dehydrogenation of n-propyl ethylbenzene. Other means have therefore been sought for the synthesis of alkyl-substituted styrenes.

One common method used in these cases consists in reacting the aromatic compound with acetaldehyde at low temperature to form a 1,1-diaryl ethane which is subsequently cracked to form equimolar amounts of the styrene and the aromatic. For example, R. A. Innes and M. L. Ocelli, AIChE 1984 Summer Natl. meeting, prepr. #42d:27p, describe the reaction of toluene with acetaldehyde at 5°–10° C. with 98% sulfuric acid as catalyst to yield 1,1-ditolylethane; the latter is cracked at 525° C. with an offretite type zeolite catalyst to yield equimolar amounts of p-methylstyrene and toluene. Similarly, EP 0168803, assigned to Nippon Petrochemical, discloses the reaction of acetaldehyde with isobutylbenzene with sulfuric acid at $-20°$ to $25°$ C. to give 1,1-bis (p-isobutylphenyl) ethane, which is cracked with protonic acids at 200°–650° C. in the liquid phase (e.g., $H_3PO_4$, $H_2SO_4$) or at 300°–650° C. in the gas phase over clays, silica-alumina or zeolites to produce the desired p-isobutylstyrene together with isobutylbenzene that must be recovered and recycled.

SUMMARY

There is provided a process for preparing a styrenic compound of the formula

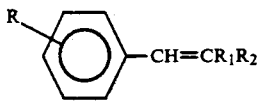

where R, $R_1$ and $R_2$ are the same or different and are hydrogen, alkyl or cycloalkyl, said process comprising contacting (i) an aromatic compound of the formula

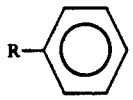

and (ii) an aldehyde of the formula $$CHO-CHR_1R_2$$

with an intermediate pore size molecular sieve catalyst under conditions sufficient to convert said aromatic compound and said aldehyde into said styrenic compound.

The alkyl groups encompassed by R, $R_1$ and $R_2$ may have, e.g., from 1 to 12 carbon atoms, and the cycloalkyl groups encompassed by R, $R_1$ and $R_2$ may have, e.g., from 6 to 12 carbon atoms. The styrenic compounds produced by this process comprise, at least predominately, the para-isomer of the formula

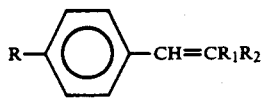

EMBODIMENTS

In accordance with a process disclosed herein, para-alkylstyrene may be prepared directly in one step by reacting alkylbenzene and acetaldehyde over a suitable molecular sieve. Molecular sieves of intermediate pore size, e.g., ZSM-5, ZSM-11, ZSM-12, ZSM-22, SAPO-11 provide a product of high p-isomer content in the production of monosubstituted styrenes.

The process disclosed herein provides for a simple, one-step method for the production of valuable styrenes from readily available starting materials. It involves the molecular sieve-catalyzed reaction of an aromatic with an aldehyde. For example, the reaction of benzene with acetaldehyde produces styrene and water. The reaction is particularly suitable for the production of substituted styrenes:

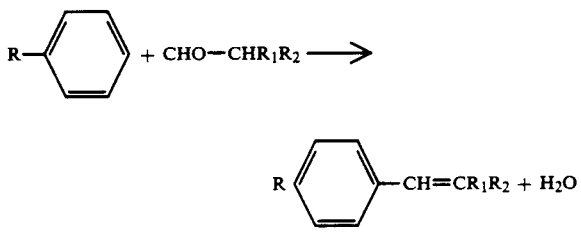

where R, $R_1$, $R_2$ are alkyl or cycloalkyl.

Representative aromatics are benzene (R=H), toluene, ethylbenzene, n- and iso-propylbenzene, n-butylbenzene, sec.-butylbenzene, isobutylbenzene, and others. Typical aldehydes are acetaldehyde, propionaldehyde, butyraldehyde, allylaldehyde, crotylaldehyde, 2-methylpropanal.

Molecular sieves useful as catalyst have a medium pore size of about 5–7A. Zeolites which are rich in $SiO_2$ (95 wt. %) and contain small amounts of Al, B, Ga, Fe and/or Cr are preferred. Especially preferred are pentasil type zeolites such as ZSM-5, ZSM-11, and ZSM-12, ZSM-22, ZSM-23, ZSM-48. Intermediate or medium pore size molecular sieve catalyst also include SAPO's such as SAPO-11, SAPO-31, SAPO-41. Catalysts of relative low activity may be desirable, e.g., those having an alpha activity of less than 50. The reaction is carried out preferably as a continuous flow reaction in a fixed bed or fluid bed reactor, at a temperature from 100°–600° C., at a pressure from about 1 to 50 atmospheres, with a feed mole ration of aldehyde to aromatic from 0.05 to 10.

EXAMPLE 1

To a fixed bed flow reactor containing 0.25 g HZSM-5 ($SiO_2/Al_2O_3$ ratio about 70), and held at a temperature of 300° C. was continuously fed a stream containing benzene and acetaldehyde in a mole ratio of 9.7 at a total LHSV of 10, together with a stream of helium of 910 ml per min. Gas chromatographic analysis of the product showed the presence of styrene, together with by-products such as ethylbenzene and ethylene.

EXAMPLE 2

The above experiment was repeated at various temperatures under the same conditions as in Example 1. The production of styrene increased with increasing temperature. The $C_7+$ liquid contained styrene in the following amounts:

| Example | Temp. °C. | % Styrene in $C_7+$ Liquid |
|---------|-----------|----------------------------|
| A | 345 | 23 |
| B | 375 | 39 |
| C | 402 | 44 |
| D | 425 | 50 |
| E | 449 | 50 |
| F | 500 | 57 |

Styrenes are valuable intermediates for the production of polymers and chemicals. For example, p-methylstyrene is a useful monomer. The present process provides a novel one-step method for the synthesis of styrenes including substituted styrenes.

What is claimed is:

1. A process for preparing a styrenic compound of the formula

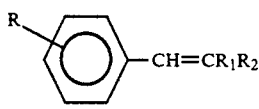—CH=CR$_1$R$_2$ where R, R$_1$ and R$_2$ are the same or different and are hydrogen, alkyl or cycloalkyl, said process comprising contacting (i) an aromatic compound of the formula

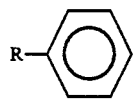

and (ii) an aldehyde of the formula

CHO—CHR$_1$R$_2$ with an intermediate pore size molecular sieve catalyst under conditions sufficient to convert said aromatic compound and said aldehyde into said styrenic compound.

2. A process according to claim 1, wherein R, R$_1$ and R$_2$ are the same or different and are hydrogen, $C_1$-$C_{12}$ alkyl or $C_6$-$C_{12}$ cycloalkyl.

3. A process according to claim 1, wherein the conversion conditions include a temperature of from 100° C. to 600° C., a pressure of from about 1 to about 50 atmospheres and a feed mole ration of said aldehyde to said aromatic compound of from 0.05 to 10.

4. A process according to claim 1, wherein said aromatic compound is selected from the group consisting of benzene, toluene, ethylbenzene, n-propylbenzene, iso-propylbenzene, n-butylbenzene, sec.-butylbenzene and isobutylbenzene.

5. A process according to claim 1, wherein said aldehyde is selected from the group consisting of acetaldehyde, propionaldehyde, butyraldehyde, allylaldehyde, crotylaldehyde and 2-methylpropanal.

6. A process according to claim 1, wherein said intermediate pore size molecular sieve catalyst is a ZSM-5 catalyst.

* * * * *